United States Patent [19]

Gessler et al.

[11] Patent Number: 4,784,267

[45] Date of Patent: Nov. 15, 1988

[54] SURGICAL SPONGE COUNTER AND DISPOSAL CONTAINER

[76] Inventors: Annette L. Gessler, 204 Fredonia Rd.; Glenda D. Saylor, 3 Meadow La., both of Greenville, Pa. 16125

[21] Appl. No.: 75,624

[22] Filed: Jul. 20, 1987

[51] Int. Cl.⁴ .............................................. B65D 85/00
[52] U.S. Cl. .................................. 206/438; 206/370; 206/561; 206/564; 206/459; 220/20
[58] Field of Search ................. 220/20; 206/370, 438, 206/561, 564, 440, 441

[56] References Cited

U.S. PATENT DOCUMENTS

| | | |
|---|---|---|
| 3,467,247 | 9/1969 | Weiss . |
| 3,469,686 | 9/1969 | Gutsche et al. . |
| 3,481,462 | 12/1969 | Chapel . |
| 3,747,751 | 7/1973 | Miller et al. . |
| 3,756,383 | 9/1973 | Kryter .............................. 220/20 X |
| 3,786,913 | 1/1974 | Crawford ........................ 220/20 X |
| 4,344,532 | 8/1982 | Eldridge, Jr. et al. ............. 206/370 |
| 4,373,629 | 2/1983 | Ulin et al. ............................ 206/350 |
| 4,501,363 | 2/1985 | Isbey, Jr. ............................. 206/570 |
| 4,541,528 | 9/1985 | Holmes ............................... 220/20 X |
| 4,572,371 | 2/1986 | Asenbauer ...................... 206/564 X |
| 4,693,371 | 9/1987 | Malpass .......................... 206/561 X |

Primary Examiner—William Price
Attorney, Agent, or Firm—Webb, Burden, Ziesenheim & Webb

[57] ABSTRACT

A container for quickly and accurately counting used surgical sponges at the conclusion of surgery having a lower half and an upper half which can be closed onto the lower half. The lower half of the container is formed with a plurality of spaced parallel walls which form a plurality of troughs to receive the used surgical sponges and alternate walls have a shorter height so that troughs on opposite sides of the alternate walls can receive either small sponges or a single large sponge. The upper half of the container has a plurality of parallel projections which are arranged to be complementary to the troughs and to extend within a portion of each trough when the upper half is closed onto the lower half.

16 Claims, 4 Drawing Sheets

SURGICAL SPONGE COUNTER AND DISPOSAL CONTAINER

BACKGROUND OF THE INVENTION

1. Field of the Invention

The invention relates to a container for the purpose of collecting, counting, weighing for blood loss and disposal of surgical sponges and more particularly to a disposable container which is adapted to receive both large and small sponges. The container may be tightly closed into a relatively sealed condition for disposal of the sponges after all of the sponges have been accounted for at the completion of a surgical procedure.

During surgical procedures, absorbent sponges are used to absorb body fluid around the site of the surgical incision. The surgical sponges are normally provided in two sizes—4"×4" gauze sponges and 14"×14" laparotomy sponges. Sponges are counted prior to the start of surgery and must be accounted for before the end of surgery. According to established standards, the 4"×4" sponges are counted in groups of 10, and the 14"×14" sponges are counted in groups of 5. In the past, used sponges have been discarded into kick buckets, removed and sorted according to size. It is essential that all of the used sponges be accounted for at the end of the surgical procedure in order to assure that no sponges have been left in the patient's body at the conclusion of surgery.

2. Description of The Prior Art

Various types of containers have been proposed in the past for receiving used surgical sponges and examples of these same containers are disclosed in U.S. Pat. Nos. 3,481,462; 3,948,390; 4,422,548; 4,234,086 and 4,361,231. Another sponge container is disclosed in U.S. Pat. No. 2,553,232 which is directed primarily to a receptacle for dental sponges. U.S. Pat. No. 3,613,890 also discloses a container for disposing of used surgical sponges. Additionally, containers for receiving used surgical sponges are disclosed in U.S. Pat. Nos. 4,190,153 and 4,312,447. All of the above enumerated patents are directed to containers for collection and disposal of surgical sponges which have drawbacks which have been overcome by applicant's invention which permits the counting and disposal of different sized sponges in a single unitary disposable container which is sealed at the conclusion of a surgical procedure and permits visually a fast and accurate counting of the used sponges after the container is closed without handling the individual sponges. Additionally, the tightly closed container of the instant invention permits the determination of the amount of blood loss during a surgical procedure since the container and sponges are weighed in the unused or clean condition prior to the surgical procedure and are weighed during or at the conclusion of the surgical procedure to determine the amount of blood the surgical patient has lost. Furthermore, the tightly closed disposable container decreases the direct contact of operating room personnel with the patient's blood which is extremely important in avoiding exposure to blood which is contaminated with acquired immune deficiency syndrome cells or hepatitis cells should the surgical patient have one of these diseases.

SUMMARY OF THE INVENTION

A principle feature of the present invention is an improved disposable sponge counting and collecting container which is simple and inexpensive to construct. The container comprises a transparent lower half or shell and a transparent upper half or shell which are formed so as to snap into a tightly closed condition at the conclusion of the surgical procedure after the used surgical sponges are placed therein. The container has a plurality of elongated troughs which are divided by upstanding walls. Alternate walls have a lesser height than adjacent walls so that the troughs formed by the walls can receive small surgical sponges and two adjacent troughs separated by a wall of lesser height can receive a laparotomy sponge which will overlie the short wall and thereby reside in two adjacent troughs. The upper half is formed with a plurality of downwardly protruding projections which are arranged to complement the troughs in the lower half of the container so that a projection fits into each trough. The projections and troughs are dimensioned in such a manner that when the upper half of the container is in the closed condition with respect to the lower half of the container, a space is left between the lower surface of a projection and the upper surface of the corresponding trough. Thus, a sponge is placed in the lower half of the container and when the upper half is closed, the sponges are firmly held in the troughs by the projections.

The sponge container is formed of a transparent plastic material such as, for example, polyvinylchloride, polyethylene, polyacrylate, polycarbonate or polyurethane and is inexpensive so that it can be disposed of with the used sponges located therein. The avoidance of high density polymer compositions is important since the upper half and the lower half may be connected along one edge by a flexible living hinge.

The instant invention has advantages over the presently used sponge counters in that it permits accurate counting of the used surgical sponges when the container is closed and provides a disposable container which is capable of being tightly closed to protect operating room personnel. Utilization of the sponge counter disclosed and claimed herein permits for the accurate counting of both large and small surgical sponges and the disposal thereof.

BRIEF DESCRIPTION OF THE DRAWINGS

The preferred embodiments of the invention are described herein in detail with reference to the accompanying drawings wherein like reference numerals refer to like elements throughout.

DESCRIPTION OF THE PREFERRED EMBODIMENTS

Figure 1:
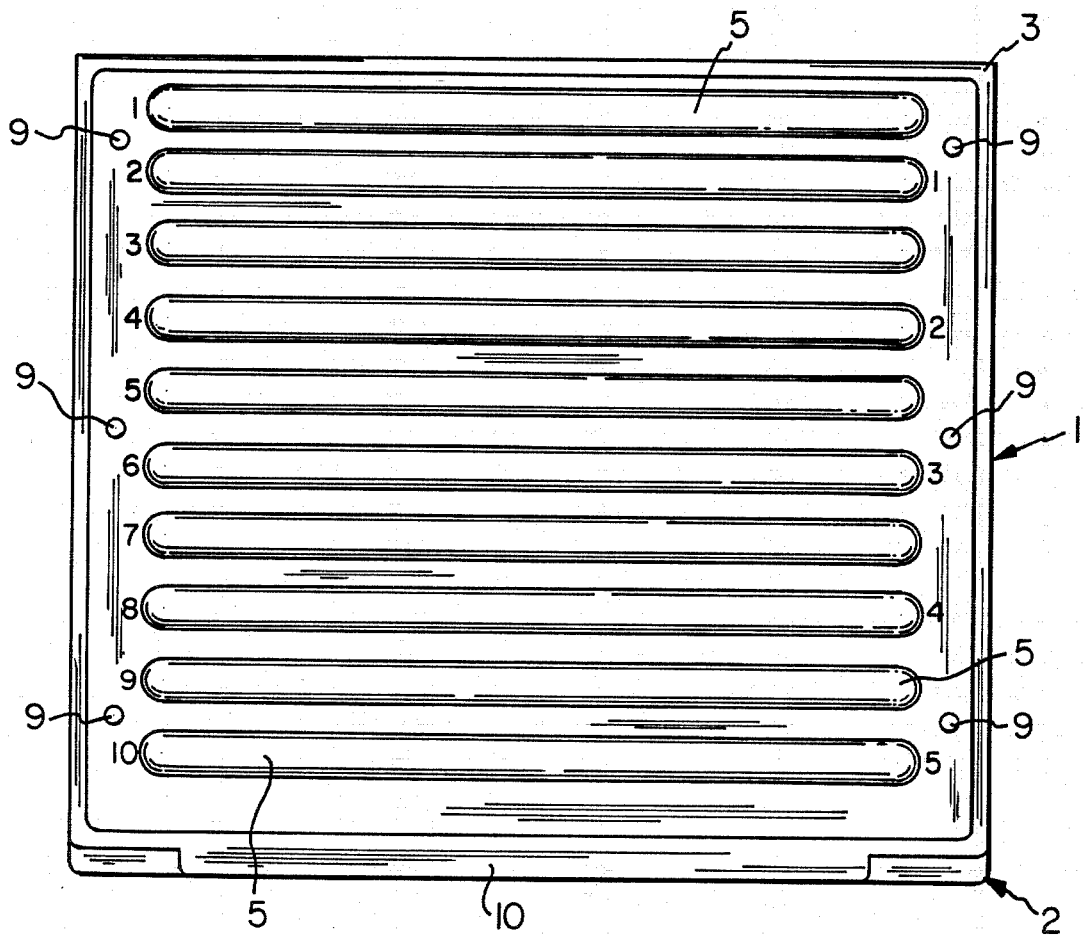
FIG. 1 is a top view of the container with the upper half in the closed position.
Figure 2:
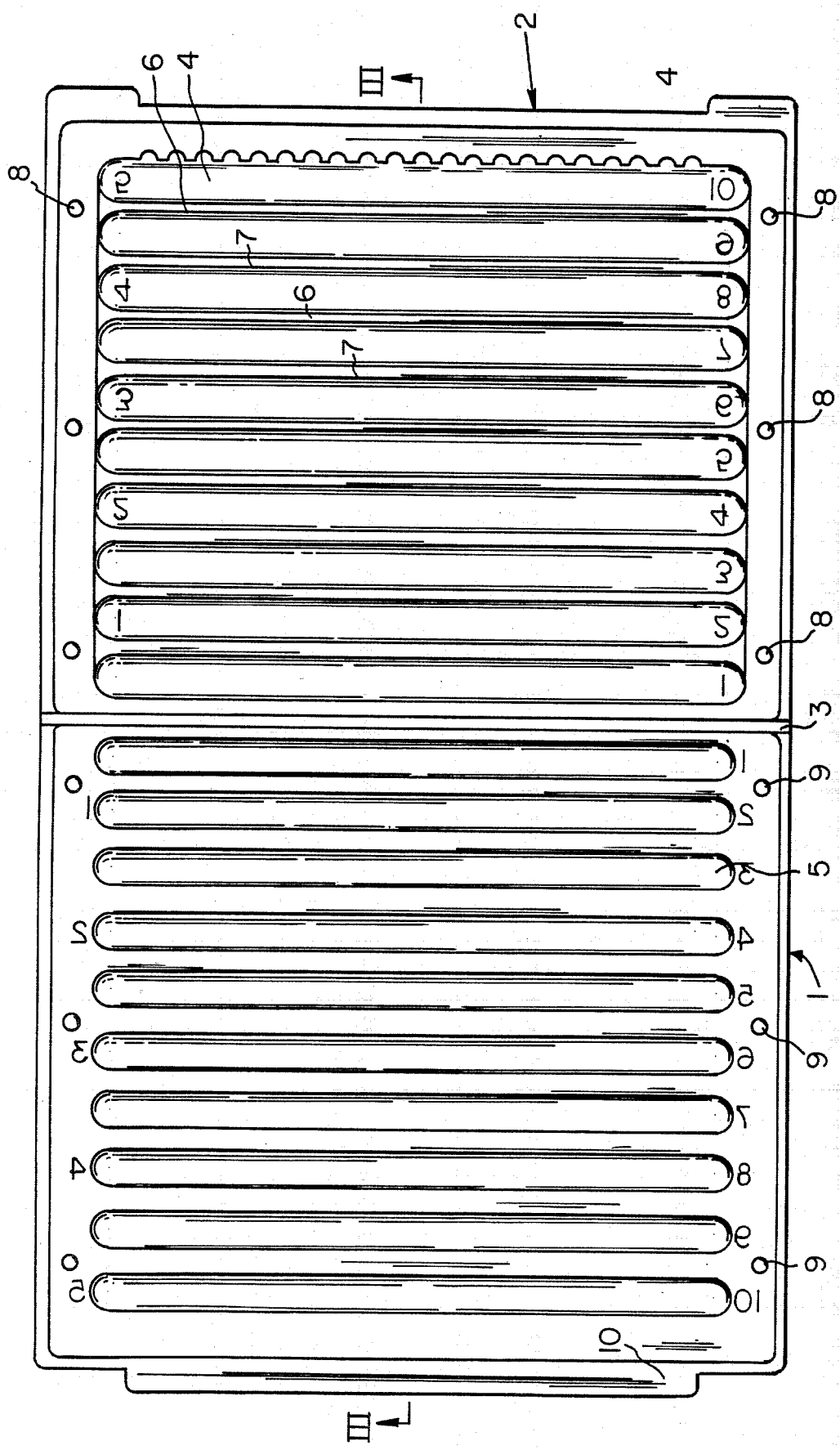
FIG. 2 is a top view of the container with the upper half in the open position.
Figure 3:
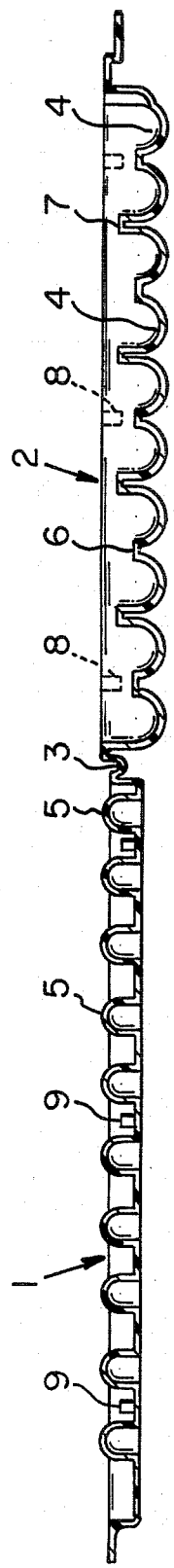
FIG. 3 is a section on line III—III of FIG. 2.

From a consideration of FIGS. 1-3 of the drawings, it will be seen that the container of this embodiment of the invention has a lower half 2 and an upper half 1. The lower half and the upper half are joined along their rear edges by a living hinge 3 which extends completely along the rear edge of the lower half and the upper half and is made from the same material as the lower half and the upper half and is integral therewith. While a living hinge is shown herein, it will be understood by those skilled in the art that other hinges can be used to connect the upper half and the lower half. However, a living hinge is preferred since it is less expensive and can be formed integrally with the upper half and the lower half which decreases the cost of manufacturing the container.

The lower half is formed with a plurality of adjacent troughs 4 which are separated by spaced walls 6 and 7. As best shown in FIG. 3 of the drawings, the walls 6 are approximately one-half the height of adjacent walls 7 for a reason to be explained hereinafter. Every other wall is a short wall 6. A plurality of substantially cylindrical recesses 8 are molded along the two side edges of the lower half and receive corresponding posts 9 which are molded along the side edges of the upper half. The upper half 1 has a plurality of downwardly extending projections 5 when it is in the closed position and each projection extends into a trough 4 to hold a sponge located in the trough in position. A tab 10 is formed on the forward edge of the upper half which is utilized to open and close the container. When the upper half is in the closed position the posts 9 frictionally interact with the recesses 8 to hold the upper and lower halves tightly closed.

The container is disposable and is made of any one of polyvinylchloride, polyethylene, polyacrylate, polycarbonate or polyurethane. The synthetic materials are relatively inexpensive which is important since the container is disposed of with the used sponges at the conclusion of a surgical procedure after the sponges are counted. Additionally, it is important that the container is transparent so that the surgical personnel can count the number of sponges in each container in order to assure themselves that no sponge has been left in the patient's body at the conclusion of surgery. By utilizing the above materials, it is possible to incorporate the living hinge into the container.

As shown in FIG. 1 of the drawings there are numerical indicia along the left side of both halves from one to ten and along the right side of each half from one to five. The reason for the numerical indicia is that when small sponges are placed in the container the numbers along the left edge are utilized and the numbers along the right edge are utilized when large sponges are placed in the container. The large sponges overlap two adjacent troughs and cover the lower walls 6 which will effectively form five large troughs in the lower half of the container. The numerical indicia on the lower half are shown in FIG. 2 of the drawings as mirror images of the numerical indicia in the lower half since the container is open. Thus, it is possible for the surgical personnel to quickly and accurately count the used sponges whether the container is right side up or upside down.

Figure 5:
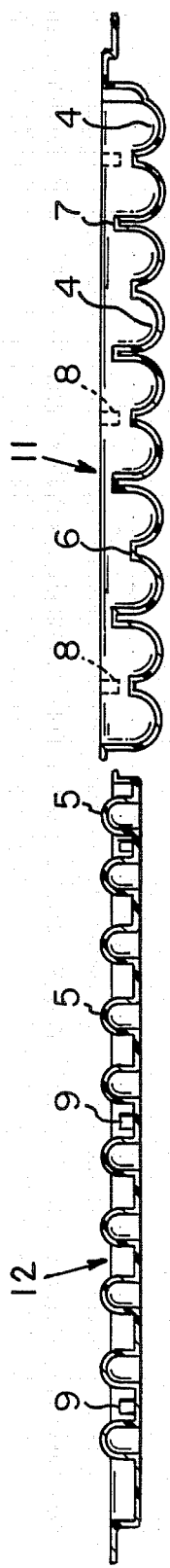
FIG. 5 is a section on line V—V of FIG. 4.
Figure 4:
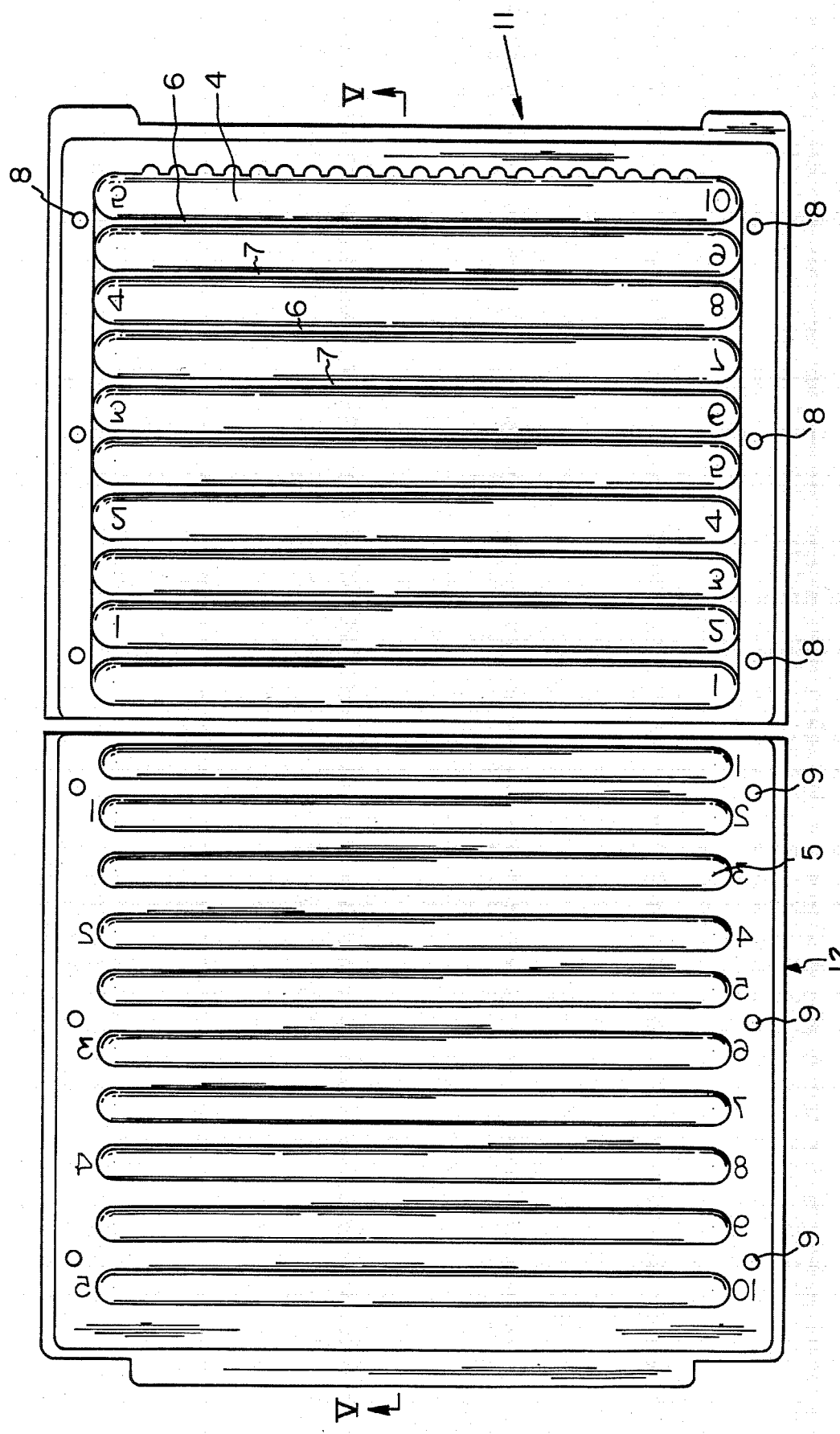
FIG. 4 is a top view of a second embodiment of the container with the upper half in the open position.

In the embodiment shown in FIGS. 4 and 5 of the drawings the lower half or shell 11 and an upper half or shell 12 are not joined along their rear edges. Thus, the upper half and the lower half of the container are two separate parts.

As in the embodiment shown in FIGS. 1–3, the lower half is formed with a plurality of adjacent troughs 4 which are separated by spaced walls 6 and 7. The walls 6 are approximately one-half the height of adjacent walls 7 and every other wall is a short wall 6. A plurality of recesses 8 are molded along the two side edges of the lower half and are adapted to receive corresponding posts 9 which are molded along the side edges of the upper half. The upper half 12 has a plurality of downwardly extending projections 5 when it is in the closed position and each projection extends into a trough 4 to hold a sponge located in the trough in position. A tab 10 is formed on the forward edge of the upper half which is utilized to open and close the container. When the upper half 12 is in the closed position the posts 9 frictionally interact with the recesses 8 to hold the upper and lower halves tightly together. The container shown in FIGS. 4 and 5 is disposable and is made of any one of polyvinylchloride, polyethylene, polyacrylate, polycarbonate or polyurethane. The container is transparent so that the surgical personnel can count the sponges in the container. As shown in FIG. 4 of the drawings there are numerical indicia along the left side of both halves from one to ten and along the right side of each half from one to five. Thus, it is possible for the surgical personnel to quickly and accurately count the used sponges.

Having described hereinabove the preferred embodiments of the present invention, it is to be understood that the invention may be otherwise embodied within the scope of the appended claims.

We claim:

1. A container for quickly and accurately counting used surgical sponges at the conclusion of surgery, said container comprising a lower half and an upper half, hinge means connecting an edge of said lower half and an edge of said upper half for closing said upper half onto said lower half, said lower half of said container having a plurality of spaced substantially parallel walls forming a plurality of troughs adapted to receive used surgical sponges, alternate walls of said plurality of walls having a shorter height than adjacent walls of said plurality of walls so that trough on opposite sides of said alternate walls are adapted to receive either small sponges or a large sponge, said upper half of said container having a plurality of substantially parallel projections arranged to be complementary to said plurality of troughs, whereby a projection on said upper half extends within a portion of each of said plurality of troughs formed on said lower half when said upper half is closed onto said lower half and means on said upper half and means on said lower half for firmly holding said upper half in the closed position on said lower half when said container is closed.

2. A container as set forth in claim 1 wherein said upper half has a handle means on the edge opposite the edge of said upper half connected to said hinge means for rotating said upper half about said hinge means.

3. A container as set forth in claim 1 wherein said hinge means is a living hinge formed of the same material as said upper half and said lower half.

4. A container as set forth in claim 3 wherein said living hinge is formed integrally with said upper half and said lower half.

5. A container as set forth in claim 1 wherein each of said plurality of troughs has a substantially U-shaped cross section and each of said projections has a substantially U-shaped cross section.

6. A container as set forth in claim 1 including numerical indicia on at least the external surface of said upper half to facilitate counting used sponges placed in said troughs.

7. A container as set forth in claim 1 wherein said upper half and said lower half are made from a transparent material.

8. A container as set forth in claim 7 wherein said transparent material is one of polyvinylchloride, polyethylene, polyacrylate, polycarbonate or polyurethane.

9. A container as set forth in claim 1 wherein said means on said upper half for firmly holding said upper half in the closed position is a plurality of posts located on said upper half and said means on said lower half for firmly holding said upper half in the closed position is a plurality of cylindrical recesses located on said lower half, whereby each of said posts extends into and frictionally engages the walls of a cylindrical recess to firmly hold said upper half on said lower half for disposal of said container with used surgical sponges contained therein.

10. A container for quickly and accurately counting used surgical sponges at the conclusion of surgery, said container comprising a lower half and an upper half, for placement onto said lower half, said lower half of said container having plurality of spaced substantially parallel walls forming a plurality of troughs adapted to receive used surgical sponges, alternate walls of said plurality of walls having a shorter height than adjacent walls of said plurality of walls so that troughs on oposite sides of said alternate walls are adapted to receive either small sponges or a large sponge, said upper half of said container having a plurality of substantially parallel projections arranged to be complementary to said plurality of troughs, whereby a projection on said upper half extends within a portion of each of said plurality of troughs formed on said lower half when said upper half is closed onto said lower half and means on said upper half and means on said lower half for firmly holding said upper half in the closed position on said lower half when said container is closed.

11. A container as set forth in claim 10 wherein each of said plurality of troughs has a substantially U-shaped cross section and each of said projections has a substantially U-shaped cross section.

12. A container as set forth in claim 10 including numerical indicia on at least the external surface of said upper half to facilitate counting used sponges placed in said troughs.

13. A container as set forth in claim 10 wherein said upper half and said lower half are made from a transparent material.

14. A container as set forth in claim 13 wherein said transparent material is one of polyvinylchloride, polyethylene, polyacrylate, polycarbonate or polyurethane.

15. A container as set forth in claim 10 wherein said means on said upper half for firmly holding said upper half in the closed position is a plurality of posts located on said upper half and said means on said lower half for firmly holding said upper half in the closed position is a plurality of cylindrical recesses located on said lower half, whereby each of said posts extends into and frictionally engages the walls of a cylindrical recess to firmly hold said upper half on said lower half for disposal of said container with used surgical sponges contained therein.

16. A container as set forth in claim 10 wherein said upper half has handle means formed on an edge for removing said upper half from said lower half.

* * * * *